United States Patent [19]

Ansari et al.

[11] Patent Number: 5,053,041
[45] Date of Patent: Oct. 1, 1991

[54] VESSEL HOLDER

[76] Inventors: Shapoor S. Ansari, 26229 East River, Grosse Ile, Mich. 48138; John T. M. Wright, 10831 Oehlmann Ave., Conifer, Colo. 80433

[21] Appl. No.: 491,727

[22] Filed: Mar. 12, 1990

[51] Int. Cl.⁵ ............................................. A61B 17/00
[52] U.S. Cl. ................................... 606/148; 606/167; 606/1; 606/150
[58] Field of Search ............... 606/148, 150, 110, 159, 606/1, 167; 128/749, 751, 757, 20

[56] References Cited

U.S. PATENT DOCUMENTS

| 4,459,978 | 7/1984 | Kotsanis | 606/150 |
| 4,582,056 | 4/1986 | McCorkle, Jr. | 601/1 |
| 4,651,733 | 3/1987 | Mobin-Uodin | 606/150 |
| 4,932,417 | 6/1990 | Off | 128/749 |

Primary Examiner—Stephen C. Pellegrino
Assistant Examiner—Gary Jackson
Attorney, Agent, or Firm—Grant L. Hubbard

[57] ABSTRACT

An improved, disposable, inexpensive vessel holder suitable for use in coronary artery surgery for impaling the cut end of a vessel graft on three sharpened wire prongs, two if that can be made to extend laterally for holding the cut end of the graft in an open position for suturing to the obstructed coronary artery, is disclosed.

16 Claims, 4 Drawing Sheets

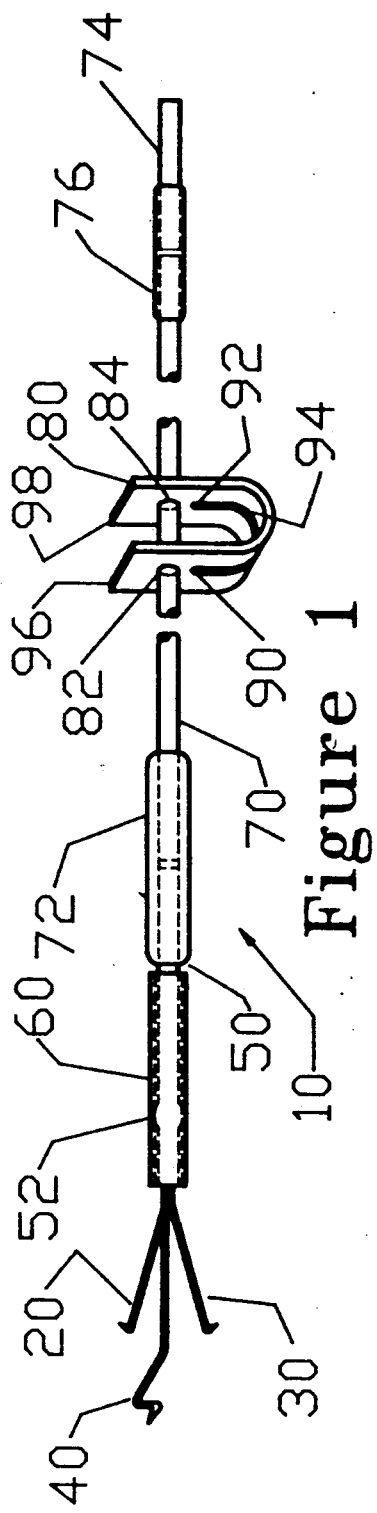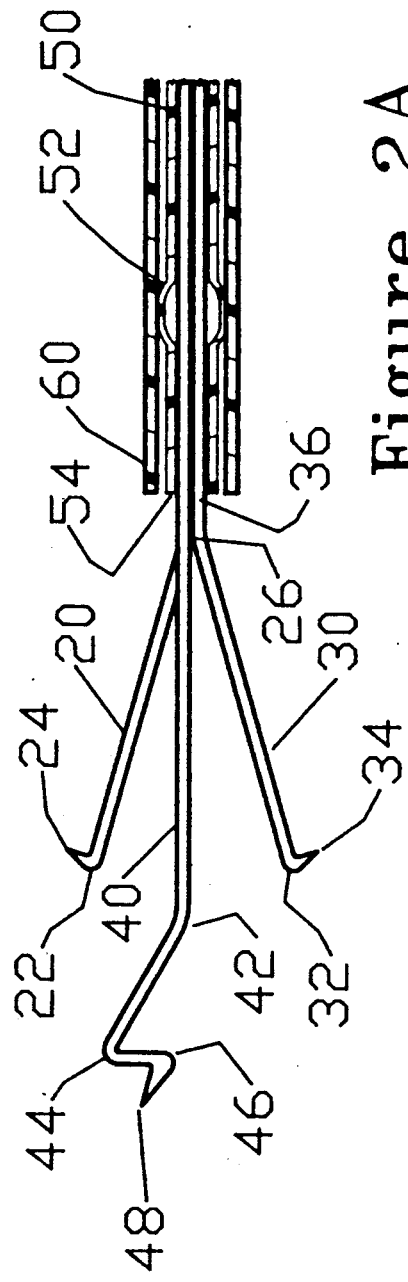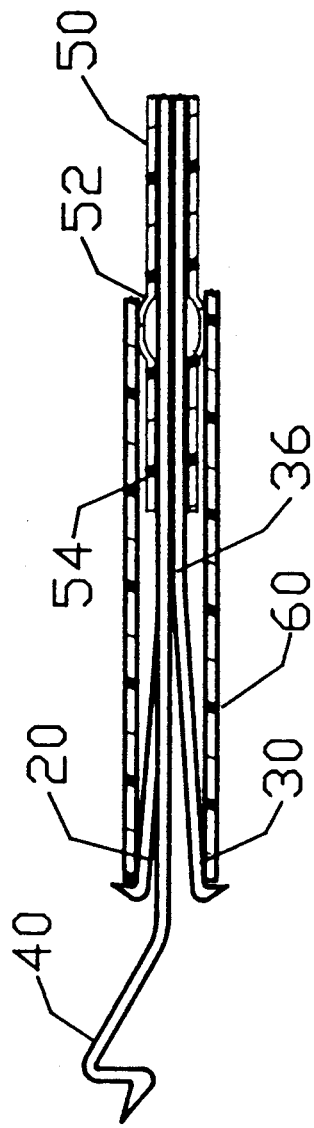

VESSEL HOLDER

BACKGROUND OF THE INVENTION

This invention relates to cardiovascular surgical instruments and comprises an improved vessel holder for use as an aid in the execution of selected cardiovascular surgical procedures, one specific application being in coronary artery bypass surgery and peripheral vascular surgery. The invention is adaptable for holding not only a vein graft, but also an internal mammary artery, bioprosthetic grafts, or synthetic grafts, such as Dacron ® or Gortex ®.

It is common surgical practice to use bypass grafts to help reestablish coronary artery circulation. In most patients one or usually more segments of the saphenous vein taken from the patient's legs, or other vessel graft, will be implanted between the aorta, near its base, and just distal to the blockage of the branch of the stenosed coronary artery. In some patients, the internal mammary artery, or another vessel graft, is also utilized for bypassing the most important coronary artery that is stenosed.

The saphenous vein is dissected free from the leg, its side branches tied off, and the vein removed. The vein graft is then washed free of blood, and cut into portions of suitable length. Each portion is then passed to the surgeon who trims the ends of the graft before anastomosing the graft to the aorta and the coronary artery. Most surgeons choose to complete all the proximal anastomoses (to the aorta) before commencing the distal anastomoses to the coronary arteries. In contrast, others choose to complete the distal anastomoses first. Regardless of the order, when undertaking the distal anastomosis to the coronary artery, it is important that the vessel graft be held steadily and adjacent to the coronary artery, with a minimum of vascular trauma and a minimum of visual and surgical obstruction by instruments in the narrow operative field.

The vessel holder, which is the subject of this invention, is intended for use as an aid to the surgeon in this circumstance by allowing the distal end of the saphenous vein or other vessel graft to be held in an open position adjacent to the coronary artery during the anastomotic procedure, without obstructing the surgeon's vision. The use of this vessel holder to hold the graft steady eliminates the use of multiple instruments, such as forceps or retractors. Forceps are commonly used to hold the angled open end of a vein graft in close proximity to the coronary artery while the cardiovascular sutures are being placed. The forceps are obstructive, difficult to hold steady, can easily slip, or cause damage to the delicate vein graft. These difficulties are minimized with the present invention.

Vessel holders are known in the art. For example such a device was described in U.S. Pat. No. 4,651,733 entitled "Blood Vessel Holding Device and Surgical Method Using Same." The disadvantage of this device is that it has to be inserted into the lumen of the vein graft, potentially causing intimal damage, and it's function ceases after only one half the anastomotic sutures have been taken. The improved vessel holder does not have these limitations.

Scanlan International company sells a Scanlan Solem vein holder, catalogue number 1001-760. This device is a pen like hollow plastic tube with a single stainless steel clip that holds the vein graft to the holder. The drawback of this device is that it is somewhat obstructive and fails securely to hold the vein.

The device that is the subject of this invention does not have these disadvantages.

It is an objective of this invention to provide a vessel holder.

It is a further objective of this invention temporarily to hold open the end of the vessel graft during anastomosis thereby to improve surgical exposure.

It is a further objective to provide an instrument that will hold open the vessel graft without traumatizing the blood contact portion of the saphenous vein or other vessel graft.

It is a further objective of this invention temporarily to hold open the end of the saphenous vein or other vessel graft in a controlled manner during anastomosis thereby to improve surgical exposure.

It is a further objective of this invention to accommodate saphenous vein or other vessel graft grafts of different sizes.

It is a further objective of this invention to provide a vessel holder with a malleable handle.

It is a further objective of this invention to provide a vessel holder with an elastic member to hold the body of the vessel graft or the graft cannula to prevent the said graft body from falling into the operative field.

It is a further objective of this invention to provide an alternative embodiment of the vessel holder such that the surgeon may choose the most suitable arrangement, depending upon the anatomy of the patient and upon whether the left anterior descending, the diagonal and the circumflex branches of the left coronary artery, or the right coronary artery is to be bypassed. The simplicity and design of the vessel holder are such that it is inexpensive and therefore may be disposable, thus eliminating the necessity of cleaning and sterilizing between uses.

Other objectives and advantages of this invention will be more apparent from the detailed description of the device that follows.

SUMMARY OF THE INVENTION

This invention is directed to a vessel holder comprising three lengths of corrosion resistant spring wire, partially covered by and retained with a close fitting clear heat shrunk plastic tube. At one end, the three wires are sharpened and angled to form three prongs. The graft is intended to be impaled on the prongs outside the anastomotic suture line and therefore retained during the placement of the anastomotic sutures. The holder is equipped with a plastic sleeve, axial movement of which causes the three prongs angularly to extend or retract. A malleable metal handle allows the hand held portion to be bent if required.

There are two preferred embodiments. The first preferred embodiment is for use when it is convenient to have the holder positioned adjacent and immediately above the graft, such as when grafting the anterior coronary arteries. In this preferred embodiment a simple elastomeric holder allows retention of the proximal portion of the graft or the graft cannula. The second preferred embodiment is intended for use when it is more convenient to have the holder located in line with but opposite the graft, e.g., when grafting the circumflex artery.

DETAILED DESCRIPTION OF THE DRAWINGS

An exemplary, presently preferred embodiment of the invention is depicted in the drawings for illustrating the principles of invention; it being understood, however, that this invention is not limited to the precise arrangements and instrumentalities shown.

FIG. 1 is an isometric, exploded view of the first preferred embodiment of the vessel occluding device, portions of the device being omitted.

FIG. 2A is an enlarged part sectional views of a first preferred embodiment of the device showing the construction of the device, with the holding portions being extended.

FIG. 2B is an enlarged part sectional views of the first preferred embodiment of the device of FIG. 2A showing the construction of the device, with the holding portions being compressed.

DESCRIPTION OF THE PREFERRED EMBODIMENT

Figure 2C:
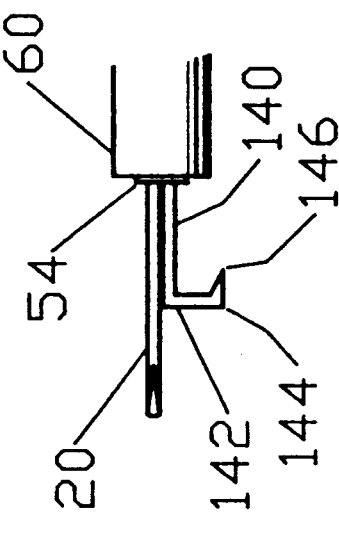
FIG. 2C is a the end of the device as depicted in FIG. 2A and 2B, with the holding portions extended, shown in reduced scale and rotated to better depict the angular relationship of the points on the hooks.

Referring to the drawings in which like numerals indicate like elements there is shown in FIG. 1 a vessel holder designated as 10, composed of three wire members 20, 30 and 40 approximately 8" long. These wire members may conveniently be made of hard drawn 0.018" diameter stainless steel wire.

Wires 20 and 30 have angled hooks formed, respectively, by bends 22 and 32 on the ends of the wires 20 and 30 which extend in opposite directions relative to each other and are sharpened to needle like points shown respectively at 24 and 34. Bends 26 and 36, respectively, are also formed in wires 20 and 30 a distance from the hooks. The bends 26 and 36 may conveniently be located approximately 0.5" from bends 22 and 32, respectively. Wires 20 and 30 are referred to as "opposed" or "opposing" wires because they comprise, respectively, oppositely directed hooks formed thereon as described.

The remaining wire 40, referred to as the central wire, is bent at 42, 44 and 46 and is the tip is sharpened to a needle-like point 48, as best shown in FIG. 2A and in FIG. 2B. The wire 40 is bent at bends 42, 44, and 46 from the axis of the central portion, shown at the right in FIGS. 1 and 2A and 2B, which roughly corresponds and is parallel to the axis of the greater part, or major portion as measured from end to end, of the instrument 10, such that the sharp needle-like point 48 lies at an angle of approximately 45° to the axis of the instrument 10. Bend 42 directs the thus bent portion of the wire between bend 42 and bend 44 at approximately 45° from the axis of the instrument, bend 44 directs the thus bent portion of the wire between bends 44 and 46 at approximately 90° from the axis of the portion between bends 42 and 44 and bend 46 directs the needle-sharp point 48 along an axis generally parallel to the axis of the portion of the wire between 42 and 44, and approximately 45° from the axis of the greater part of the instrument, abbreviated hereinafter as the greater axis of the instrument.

The three wires are affixed in apposition by a suitable heat shrinkable tubing 50 proximate the bends previously discussed and 74 and by a metal canula 70, the latter two of which will be discussed later. The tubing 50 is, in an exemplary embodiment, a 3/64" diameter irradiated polyolefin which is heat shrunk along all or most of its length except for a portion 52 which is spaced from the end 54 which is proximate the bends. The un-shrunk portion 52 is, of course, larger than the shrunk portions, the shrunk portions serving to secure the wires 20, 30 and 40 in a fixed relation to each other such that the points thereon are directed as previously described.

A length of tubing 60 which has an inside diameter larger than the outside diameter of the shrunk portions of tube 50 but smaller than the outside diameter of unshrunk portion 52 of tube 50 is slidably received over tube 50 and portion 52, the un-shrunk portion 52 be forcibly compressed slightly and, thereby, forming a high friction slidable interface between the interior of tube 60 and un-shrunk portion 52 of tube 60. Thus, a sliding concentrically placed tube 60 resides by reason of a friction fit over the underlying tube 50. Tube 60 may conveniently be a 1.5" length of a hard grade of polyurethane 0.068" inside diameter, 0.098" outside diameter.

The bend 42 in wire 40 lies a convenient distance, approximately 0.125" to 0.5", beyond bends in wires 20 and 30. The length of heat shrinkable tube 50 may conveniently be approximately 2.5", extending toward the distal end of the device to a point proximate an end of a malleable metal tube 70, which is bonded to the heat shrunk tube 50 by a larger heat shrunk sleeve 72. While not essential to functionallity, it is preferred that the tube 50 extend into the metal tube 70 from one-half to one inch. The malleable metal tube 70 extends toward the distal end of the instrument 10 where it terminates proximate the end of another section 74 of heat shrunk polymer tubing, such as that previously described respecting tubing 50, to which it is bonded by a heat shrunk sleeve 76. Again, it is preferred that the tube 74 extend into the metal tube 70 from one-half to one inch. The length of heat shrinkable tube 76 may conveniently be 1.5". Alternatively, of course, the tube 50 may extend to the distal end of the device, in which case tube 70 is omitted.

The malleable metal tube 70, such as a 5.62" length of 0.064" inside diameter and 0.094" outside diameter annealed stainless steel, forms a simple handle.

The sleeves 72 and 76 may conveniently comprise of 1.5" lengths of 3/32" diameter irradiated polyolefin heat shrinkable tubing. The end of sleeve 72 may also form a stop to limit the movement of sleeve 60.

A vein holder 80, which may be in the form of a U or a cylinder, or in another configuration, is mounted on malleable metal tube 70, or on heat shrunk tube 50 if a metal tube is not used. The tube 70, or tube 50, passes through aligned holes 82 and 84 in the vein holder 80. The holder 80 may conveniently be die cut from a 0.062 thick sheet of silicone rubber. The holes 82 and 84, being smaller in diameter than the tube 70, results in a slidable friction fit causing the holder to be firmly held, unless forced to move, but slidably moveable on tube 70, or tube 50. Vein holder contains another pair of aligned holes 90 and 92, connected by a slot 94, which is constructed and configured to hold vein graft.

Returning to FIGS. 3A and 3B, a second preferred embodiment of the invention is depicted. The second preferred embodiment is identical in all respects to the first preferred embodiment shown in FIGS. 2A and 2B, except that the wire 40 is replaced with a wire 140 which has bends 142 and 144 and a sharpened point 146. The bends 142 and 144 result in a reverse hook, i.e. a hook which is directed away from the proximal end of the instrument substantially parallel to the greater axis of the instrument and the axis of the major portion of wire 140 which, like wire 40, extends to the distal end of the instruments through tube 50 or through tubes 50, 70 and 74 as described.

In use, following the removal and preliminary preparation of the saphenous vein from the patient's leg the vein grafts will be cut into appropriate lengths. The distal end of saphenous vein graft will be cut an appropriate angle and trimmed to leave a small ear-like protrusion on either side, and a nose-like protrusion on central portion of the graft. The ear-like and nose-like protrusions will lie just outside the suture line of the completed anastomosis.

Figure 5:
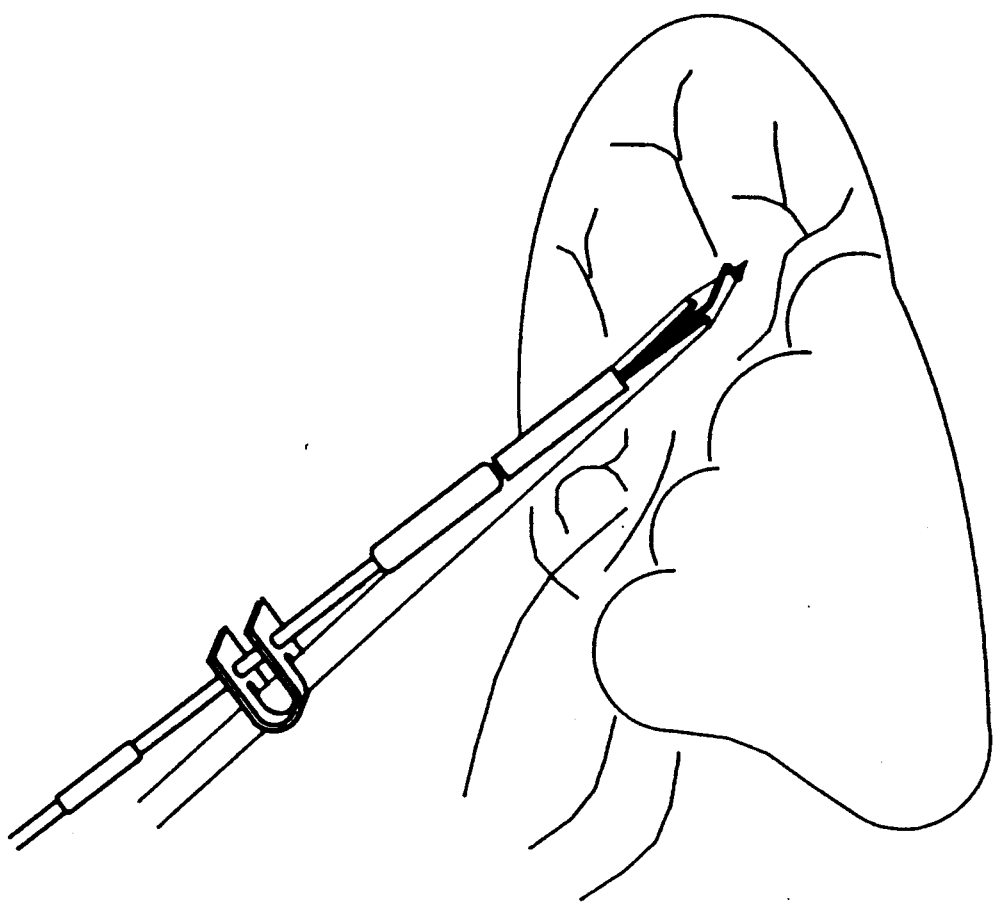
FIG. 5 is an isometric view showing the first preferred embodiment in use.

Referring to FIG. 5 in particular, and to FIGS. 2A and 2B, with the holder prongs in the retracted position as shown in FIG. 2B the cut end of the vein graft will then gently be impaled on the prongs, so that the point 48 of the central prong 40 pierces the nose-like protrusion, and the points 24 and 34 of each of the lateral prongs 20 and 30 pierces an ear-like protrusion outside the intended line of the anastomosis. The sleeve 60 is then gently slid distally toward the handle formed by tube 70, or a continuation of tube 50, to extend the prongs in an angular outwardly direction as shown in FIG. 5, and therefore open out the cut end of the graft. The sleeve 60 is moved just a sufficient distance to extend the prongs sideways the required amount to open the graft. The friction fit between sleeve 60 and the un-shrunk diameter 52 of tube 50 is sufficient to prevent unwanted movement occurring due to the spring force of the prongs, which inherently have a tendency to exert a force tending to move the sleeve 60 in the distal direction, i.e. to the right as one views FIG. 1.

Meanwhile cardiopulmonary bypass will have been established and the heart will usually be immobilized by cross clamping the base of the aorta, and perfusing cold cardioplegia solution into the coronary arteries via the aortic root. The surgeon makes a suitable incision into the lumen of the coronary artery to be bypassed, distal to the coronary occlusion, and elongates the incision as required. The vein graft mounted on the vessel holder will have been handed to the surgeon's assistant, who, using the vessel holder, will position the cut end of the vein graft immediately above and next to the anastomotic incision in the coronary artery. The angle of the needle-like prong 48 on the central wire prong 40 is such that the holder may be held against the surface of the flaccid heart, without the sharp point 48 of wire 40 impinging on the epicardium.

Figure 3B:
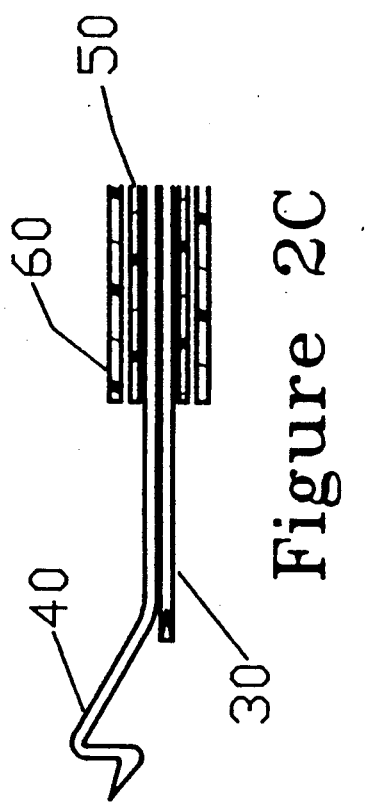
FIG. 3B is an enlarged part sectional views of the second preferred embodiment of the device of FIG. 3A showing the construction of the device, with the holding portions being compressed.
Figure 3A:
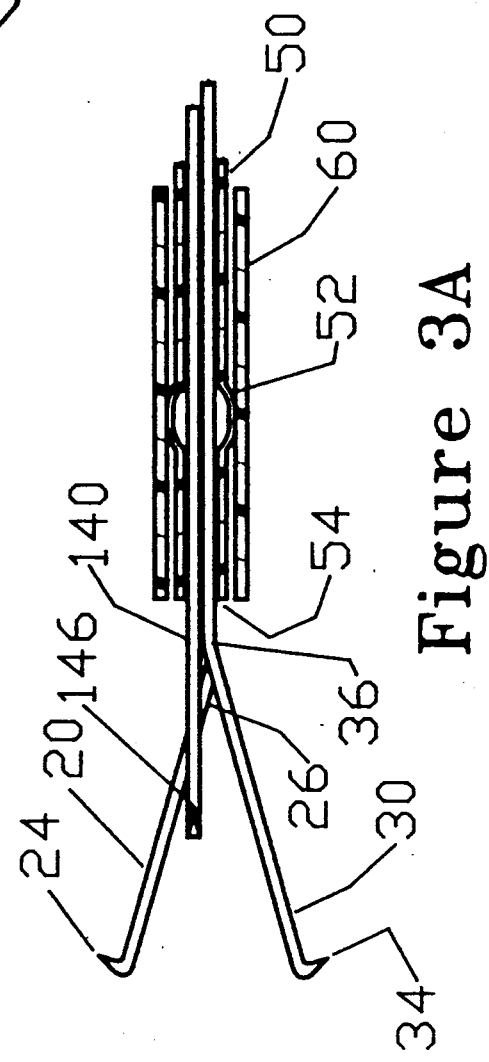
FIG. 3A is an enlarged part sectional views of a second preferred embodiment of the device showing the construction of the device, with the holding portions being extended.
Figure 4:
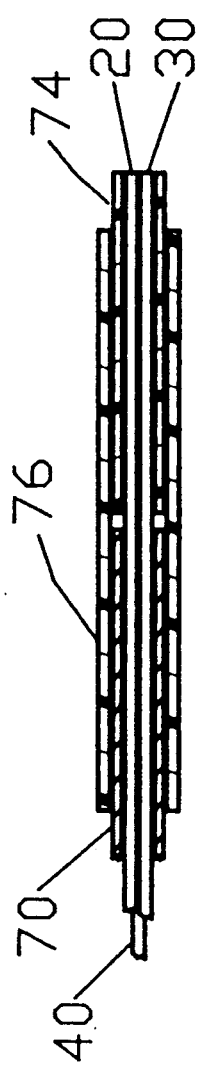
FIG. 4 is an enlarged part sectional view of part of the central portion of the device showing the bonding of a metal canula to a shrunk polymer canula using a shrunk polymer sleeve.
Figure 6:
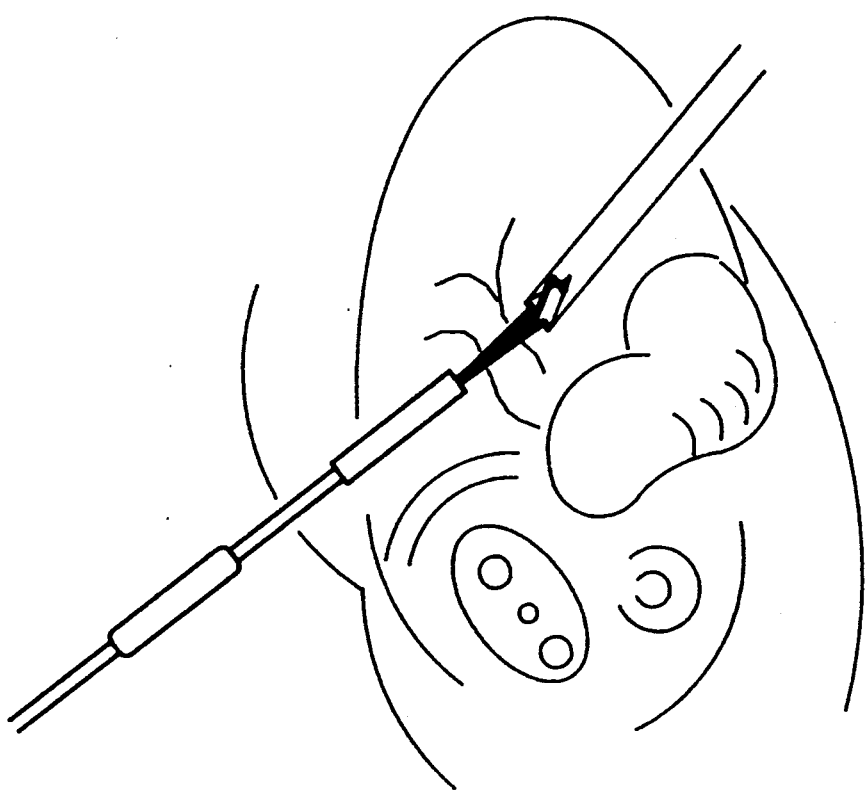
FIG. 6 is an isometric view showing the second preferred embodiment in use.

Referring now to FIGS. 6 and 3A and 3B, the second preferred embodiment of the device of this invention is used in a similar manner, except that the surgeon's assistant use the embodiment of FIGS. 3A and 3B to impale the end of the graft vessel and pull it, rather than to push it as is the case with the embodiment of FIGS. 2A and 2B, toward the anastomotic incision, as shown in FIG. 6.

In addition, if required by the patient's anatomy, the malleable tubular handle member 70 may be bent appropriately so that the assistant may conveniently hold the vein graft in the optimum position during the anastomotic procedure. When appropriate, and it desired by the surgeon, the proximal portion of the vein graft, or vein graft cannula if a cannula is used, may be inserted in the vein holder to keep the graft vessel from falling into the operative field. This may be achieved by compressing the upwardly directed ends 96 and 98, as viewed in FIG. 1, between the thumb and forefinger. This force causes the slot 94 to open, after which the flattened graft may be gently inserted into the slot. Releasing the digital force on ends 96 and 98 causes the slot to re-close, gently gripping the graft in the apertures 90 and 92.

At the completion of the anastomosis the vessel holder is removed from the graft by firmly holding the malleable tube 70 and sliding member 60 proximally toward the anastomosis. This action causes wire prongs 20 and 30 to move in an inwardly direction. The sharp needle-like prongs 24 and 34 on wire members 20 and 30 and the prong 48 on wire 40 are then disengaged from the graft and the holder removed from the operative field.

What is claimed is:

1. A generally cylindrical elongate vessel holder, having a generally linear center line, for holding a vessel graft during bypass surgery comprising three sharp wire prongs on which the cut end of the graft may be impaled, two of which prongs extend outwardly from the center line and one of which prongs extends substantially along the center line.

2. The vessel holder of claim 1 further comprising a malleable metal tube which is generally coaxial with the center line extending from proximate one end to proximate the other end of the instrument forming a bendable handle.

3. The vessel holder of claim 2 in which malleable handle is retained in position by one or more lengths of heat shrunk tubing.

4. The vessel holder of claim 1 further comprising a vein holder comprising an elastic member so constructed and disposed as to be slidable toward the respective ends of the instrument.

5. The vessel holder of claim 4 wherein the vein holder comprises a substantially flat sheet having formed therethrough at least two holes for securing the vein holder as part of the instrument and a slot for receiving the graft.

6. The vessel holder of claim 1 in which the wires are between 0.010 and 0.060" diameter.

7. A generally cylindrical elongate vessel holder, having a generally linear center line, for holding a vessel graft during bypass surgery comprising two sharp wire side prongs and a sharp central prong, on which the cut end of the graft may be impaled, the central prong extending axially beyond the two side prongs.

8. A generally cylindrical elongate vessel holder, having a generally linear center line, for holding a vessel graft during bypass surgery comprising of two sharp wire side prongs and a sharp wire central prong on which the cut end of the graft may be impaled, the central prong constructed and disposed to lie between the two side prongs and adjacent the holder.

9. A generally cylindrical elongate vessel holder, having a generally linear center line, for holding a vessel graft during bypass surgery comprising of three sharp wire prongs, on which the cut end of the graft may be impaled and heat shrunk tubing holding the wire prongs together.

10. The vessel holder of claim 9 further comprising a sliding member received on the heat shrunk tubing for causing wire members to extend outwardly from the center line of the instrument thereby opening end of the graft a controlled amount.

11. The vessel holder of claim 10 wherein the sliding member is maintained by slidable frictional contact with the heat shrunk tubing by a section of the heat shrunk member that is not fully heat shrunk.

12. A vessel graft holder (10) comprising three wire members (20, 30 and 40), two of the wires (20 and 30) having angled hooks formed thereon, respectively, by bends 22 and 32 on the ends thereof, the hooks extending in opposite directions relative to each other and being sharpened to needle like points (24 and 34), and having bends therein (26 and 36) a distance from said hooks, the third wire (40) having first, second and third bends (42, 44 and 46) and having a sharpened tip (48), the bends (42, 44 and 46) being so formed that the sharp needle-like point (48) lies at an angle of approximately 45° with respect to the wire (40) immediately before the first bend (42), the wires being secured into a bundle by heat shrunk tubing (50).

13. The vessel graft holder of claim 12 further comprising a malleable metal canula (70) forming a bendable handle.

14. The vessel graft holder of claim 12 wherein a portion (52) of the shrunk tubing (50) which secures the wires is not fully heat shrunk and further comprising a compression tube (60) which has an inside diameter larger than the outside diameter of the shrunk portions of the heat shrunk tubing (50) but smaller than the outside diameter of un-shrunk portion (52) slidably received over tube 50 and portion 52, the un-shrunk portion (52) of the tubing forming a high friction slidable interface between the interior of tube compression tube (60) and un-shrunk portion (52) of tube 50, the compression tube (60) being moveable from a first position compressing the ends of the wires together to a second position perming the ends of the wires to expand outwardly and angulary from the center line of the graft holder.

15. The vessel graft holder of claim 12 further comprising a vein holder (80) in the form of a U mounted by slidable friction fit for movement along the length of the wires, the vein holder having formed therein at least one opening for receiving and holding a vein graft.

16. A vessel graft holder (10) comprising three wire members (20, 30 and 40), two of the wires (20 and 30) having angled hooks formed thereon, respectively, by bends 22 and 32 on the ends thereof, the hooks extending in opposite directions relative to each other and being sharpened to needle like points (24 and 34), and having bends therein (26 and 36) a distance from said hooks, the third wire (140) having first and third bends (142 and 144 and having a sharpened tip (146), the bends (142 and 144) being so formed that the sharp point (146) extends distally of the instrument approximately parallel to the wire (140) immediately before the first bend (142), the wires being secured into a bundle by heat shrunk tubing (50).

* * * * *